United States Patent [19]

Hillion et al.

[11] 3,946,087

[45] Mar. 23, 1976

[54] PROCESS FOR HYDROGENATING KETONES

[75] Inventors: Gerard Hillion, Franconville; Christian Lassau, Villepreux, both of France

[73] Assignee: Institut Francais du Petrole des Carburants et Lubrifiants, Paris, France

[22] Filed: Mar. 6, 1974

[21] Appl. No.: 448,483

[30] Foreign Application Priority Data

Mar. 12, 1973 France .............................. 73.08775

[52] U.S. Cl. ..................... 260/631 H; 260/638 B
[51] Int. Cl.² C07C 29/00; C07C 31/00; C07C 31/02
[58] Field of Search ..................... 260/631 H, 638 B

[56] References Cited
UNITED STATES PATENTS

| 1,247,629 | 11/1917 | Brochet ........................ 260/631 H |
| 2,158,040 | 5/1939 | Blumenfeld ..................... 260/638 B |
| 3,052,730 | 9/1962 | Eschinasi ....................... 260/638 B |
| 3,412,174 | 11/1968 | Kroll ............................... 260/683.9 |
| R20,447 | 7/1937 | Schrauth ........................ 260/638 A |

*Primary Examiner*—R. Gallagher
*Assistant Examiner*—D. B. Springer
*Attorney, Agent, or Firm*—Millen, Raptes & White

[57] ABSTRACT

Ketones are converted by hydrogenation to the corresponding secondary alcohols, in the presence of a soluble catalyst which is obtained by contacting a metal compound, for example a cobalt, nickel or iron salt, with a reducing agent, preferably a trialkylaluminum compound, the reaction being carried out with added metal alcoholate, preferably an alkali metal alcoholate.

11 Claims, No Drawings

PROCESS FOR HYDROGENATING KETONES

The invention concerns a process for producing secondary alcohols by catalytic hydrogenation of the corresponding ketones.

Catalytic compositions obtained by contacting one or more metal compounds with one or more reducing agents have already been described. The catalyst could be used for hydrogenating ketones.

A substantial improvement results from employing additives such as hereinafter described.

The catalytic composition used according to the invention results from contacting one or more metal compounds with one or more reducing agents and at least one metal alcoholate.

The metal compounds are selected from the compounds of metals from groups Ib, IIb, IVa, Va, VIa, VIIa and VIII, such as, for example, titanium, vanadium, chromium, manganese, iron, cobalt, nickel, copper, zinc, zirconium, molybdenum, ruthenium, rhodium, palladium, tungsten, iridium or platinum. The associated ions are either inorganic anions, such as hydride, halide or sulfocyanide ions, or organic anions such as alkoxide ions, for example acetylacetonate, cyclopentadienyl ions or sulfonate ions, for example camphorsulfonate. They can also be obtained from organic acids, for example carboxylic acids such as stearic, 2-ethyl hexanoic, decanoic or naphthenic acids. Examples of metal compounds which can be used according to the process of the invention are: cobalt bromide, naphthenate, oleate, stearate, octoate or decanoate (irrespective of the effective cobalt content), iron chloride, chromium acetylacetonate, dichlorodicyclopentadienyl titanium, bis-tricyclohexyl phosphine cobalt dibromide, manganese chloride, iron stearate, molybdenum carboxylates or nickel octoate. Anions which do not react with the reducing agent and which are soluble in the reaction mixture are preferred.

The reducing agents are preferably organic derivatives of boron or aluminum, or organo lithium compounds of the formula R-Li in which R is a monovalent hydrocarbon radical optionally substituted with atoms or radicals which do not participate to the reaction.

The following compounds are preferably used:

1. Those of the formula Al $H_nX_{3-n}$ in which $n$ is zero (only if $X = R$), 1, 2 or 3 and the similar or dissimilar X groups are selected from R, OR, $NR_2$, NHR or SR groups in which R is a monovalent substituted or unsubstituted, linear or cyclic hydrocarbon radical, which radical may contain heteroatoms such as oxygen, nitrogen, sulfur or metals. R may be, for example, an alkyl, cycloalkyl or aryl radical. When $n = 1$, two groups R may be linked so as to form an -A-Z-B- group wherein A and B are alkylene groups and Z is an oxygen or sulfur atom, an alkylene group, a NH— group or a N-hydrocarbyl group.

2. Those of the general formula M $[AlH_mX'_{4-m}]_p$ in which $m$ is 1, 2, 3 or 4; M is a mono- or di-valent metal selected from the groups Ia and IIa and $p$ is the valence of this metal.

The similar or dissimilar X' groups are selected from the groups R, OR, $NR_2$, NHR and SR in which R is as hereinbefore defined. Two groups R may be linked as above indicated.

Useful reducing agents according to the present invention are for example:

Li Al H (O-tert-butyl)$_3$, Na Al H (O-tert-butyl)$_3$, Al H (O-tert-butyl)$_2$, Na Al H $(C_2H_5)_3$, Al $(C_2H_5)_3$, Al (iso $C_4H_9)_3$, Al H (iso $C_4H_9)_2$, Na Al $H_4$, Li Al $H_4$, Na Al $H_2$ (O $CH_2CH_2$ O $CH_3)_2$, Na Al H $(OC_2H_5)_3$, Li Al H $(C_2H_5)_3$, $C_4H_9Li$, Li Al $H_2$ (O-tert-butyl)$_2$, Li Al $H_2$ (O-tert-butyl) (O-tetrahydrofurfuryl).

The third constituent of the catalytic system is a metal alcoholate, for example sodium or lithium ethylate, iso-propylate or tert- butylate. The molar ratio of the alcoholate to the metal compound is in the range of from 0.1 to 10. It is preferably selected from 0.5 to 5.

The alcoholate has preferably the formula

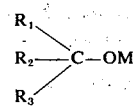

in which M is an alkali metal, for example Na, Li or K. $R_1$, $R_2$ and $R_3$ are selected from hydrogen and the hydrocarbon monovalent radicals; two radicals, for example $R_1$ and $R_2$, may also be linked so as to form a ring with the adjacent carbon atom. The preferred alcoholate is that obtained from the alcohol to be produced.

Depending on the particular metal compound and associated reducing agent, the molar ratio of the reducing agent to the metal compound is variable. It is usually from 0.1 to 20 and preferably from 0.2 to 6.

The reaction is carried out in the range of from 25° to 300°C. The catalytic composition is usefully prepared at a lower temperature.

The concentration of the metal employed may be as low as 0.0001 g per 100 g of charge. The preferred concentrations range from 0.001 to 1 g of metal per 100 g of charge.

The reaction is carried out in the liquid phase optionally in the presence of a solvent with the purpose of maintaining the reaction temperature at the desired value and retaining the catalyst in this phase when removing the reaction product. The catalyst may be supported on a carrier such as alumina, silica, alumina-silica or active carbon. In that case, the active metal content of the catalyst ranges approximately from 0.1 to 10% by weight, depending on the activity of this metal.

The hydrogen partial pressure may range from 0.1 to 100 bars.

The ketones to be used have the formula R — CO — R' in which R and R' are monovalent hydrocarbon radicals or constitut a bivalent radical forming a ring with the —CO— group. We can mention, as non-limitative examples: acetone, acetophenone, cyclopentanone, cyclohexanone, cyclododecanone, methylisobutyl ketone, benzophenone, piperitone, menthone and pulegone. The preferred ketones are unsubstituted or substituted with groups which do not react with hydrogen and do not poison the catalyst. A simple preliminary test makes it possible to determine whether a given ketone satisfies these conditions or not.

The following examples illustrate the invention without limiting the scope thereof.

EXAMPLE 1

For converting 137 g of menthone to menthol, by hydrogenation, we use 2.5 milliatoms of nickel in the form of the octoate which is reduced with 7.5 millimoles of triethylaluminum. We add 10 millimoles of sodium mentholate and the autoclave is finally charged with hydrogen at 115°C under a pressure of 20 bars. The reaction is continued for 3 hours.

Menthol is obtained in a quantitative yield.

EXAMPLE 2

Example 1 is repeated, except that sodium mentholate is not used. After 3 hours, the conversion is only 20%.

EXAMPLE 3

Example 1 is repeated, except that 0.75 millimole of triphenylphosphine is present during the reduction. The reaction is terminated in 1 hour and menthol is obtained in a quantitative yield.

EXAMPLE 4

Example 3 is repeated, except that no sodium mentholate is present. Menthol is obtained in a quantitative yield but the reaction is terminated after 4 hours only.

Examples 1 to 4 show that the addition of a sodium salt greatly increases the rate of the hydrogenation reaction, even when the latter is carried out in the presence of a phosphine.

EXAMPLE 5

Example 1 is repeated, except that the reducing agent consists of 2.5 millimoles of Na Al $H_4$. The reaction is terminated after 3 hours and menthol is obtained quantitatively.

EXAMPLE 6

Example 5 is repeated, except that we add 0.75 millimole of triphenylphosphine during the reduction. The reaction is terminated after 2 hours and menthol is obtained in a quantitative yield.

EXAMPLE 7

Example 6 is repeated, except that piperitone is used as starting material. The hydrogenation of piperitone to menthone takes 5 minutes, while the hydrogenation to menthol takes 2 hours.

This example shows that the catalyst of the invention may hydrogenate unsaturated ketones to the corresponding saturated alcohols.

EXAMPLE 8

Example 1 is repeated with methyl isobutyl ketone and the sodium derivative of methylisobutylcarbinol as starting materials. The reaction is terminated after 2.5 hours; methylisobutylcarbinol is obtained in a quantitative yield.

EXAMPLE 9

Example 1 is repeated with acetone and sodium isopropylate. After 3 hours at 80°C and a pressure of 20 bars, the reaction is terminated. Isopropanol has been obtained in a quantitative yield.

EXAMPLE 10

Example 1 is repeated, except that we use 5 milliatoms of iron in the form of the octoate reduced with 15 millimoles of triethyl aluminum. After 4 hours we obtain menthol in a quantitative yield.

EXAMPLE 11

Example 1 is repeated, except that we use cyclohexanone and sodium cyclohexanolate. After 3 hours, the hydrogen is no longer absorbed and cyclohexanol is obtained in a quantitative yield.

EXAMPLE 12

Example 1 is repeated, except that we use 3 milliatoms of cobalt in the form of stearate, reduced with 10 millimoles of triethylaluminum. The reaction is terminated after 4 hours and menthol is obtained in a quantitative yield.

We claim:

1. In a process for converting a ketone of the formula R — CO — R' where R and R' are monovalent hydrocarbon radicals or, when taken together, are a divalent hydrocarbon radical, to form the corresponding secondary alcohol, said process comprising reacting said ketone in the liquid phase with free hydrogen in the presence of a catalyst obtained by reacting a molar proportion of at least one compound (A) of a metal from one of the groups Ib, IIb, IVa, Va, VIa, VIIa or VII of the periodic classification, with a 0.1–20 molar proportion of a metal reducing compound (B) selected from the group consisting of a. a compound of the formula R-Li where R is a monovalent hydrocarbon radical, b. a compound of the formula AlH$n$ X $_{3-n}$ where $n$ is zero provided all X are R groups, or 1, 2 or 3, X is R, OR, NR$_2$, NHR or SR or, provided $n$ is 1, two R groups are linked to form an -A-Z-B- group where A and B are alkylene groups and Z is an oxygen or sulfur atom, an alkylene group, a NH group or N-hydrocarbyl group, and R is a monovalent hydrocarbon radical, and c. a compound of the formula M (AlH$m$ X' $_{4-m}$)$_p$ where $m$ is an integer from 1 to 4, M is a mono- or di-valent metal selected from the metals of groups Ia and IIa, $p$ is the valence of this metal and X' is defined as X, the improvement wherein said reacting of said ketone with hydrogen in the presence of said catalyst is conducted in the additional presence of, as part of the catalyst system, 0.1–10 molar proportion of at least one metal alcoholate of the formula

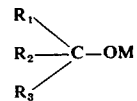

where M is an alkali metal and R$_1$, R$_2$ and R$_3$ are hydrogen atoms or monovalent hydrocarbon radicals or, when taken by pairs, form a hydrocarbon ring with the carbon atom linked to the —OM group, the hydrocarbon portion of said metal alcoholate being aromatic of not more than 13 carbon atoms, or alkyl or cycloalkyl of not more than 12 carbon atoms with the provision that said cycloalkyl contains at least 5 carbon atoms.

2. A process according to claim 1 wherein the metal compound (A) is a cobalt, nickel or iron salt.

3. A process according to claim 1 wherein the metal compound (A) is a cobalt, nickel or iron carboxylate.

4. A process according to claim 1 wherein the metal compound (B) is butyl lithium.

5. A process according to claim 1 wherein the metal compound (B) is of the formula Al X$_3$ where X is a monovalent hydrocarbon radical.

6. A process according to claim 1 wherein the metal alcoholate is a sodium alcoholate.

7. A process according to claim 1 wherein the molar proportion of metal alcoholate is 0.5–5.

8. A process according to claim 1 wherein the molar proportion of metal compound (B) is 0.2–6.

9. A process according to claim 1 wherein there is used from 0.001 to 1 part by weight of metal of the compound (A) per 100 parts by weight of ketone.

10. A process according to claim 1 wherein said converting is carried out at 25°–300° C. under a hydrogen pressure of 0.1–100 bars.

11. A process according to claim 1 wherein the metal alcoholate is one formed with the secondary alcohol corresponding to the ketone to be converted.

* * * * *